United States Patent [19]

Harvey

[11] 4,238,476
[45] Dec. 9, 1980

[54] DENTIFRICES

[75] Inventor: Kenneth Harvey, Wilmslow, England

[73] Assignee: Colgate Palmolive Company, New York, N.Y.

[21] Appl. No.: 37,597

[22] Filed: May 10, 1979

[30] Foreign Application Priority Data

May 19, 1978 [GB] United Kingdom ............... 20758/78

[51] Int. Cl.$^3$ .............................................. A61K 7/18
[52] U.S. Cl. ...................................... 424/52; 424/49; 424/56; 424/57
[58] Field of Search ..................................... 424/49–58

[56] References Cited

U.S. PATENT DOCUMENTS

| | | | |
|---|---|---|---|
| 2,054,742 | 9/1936 | Elbel | 424/53 |
| 3,538,230 | 11/1970 | Pader et al. | 424/54 |
| 3,662,059 | 5/1972 | Wiesner et al. | 424/52 |
| 3,927,202 | 12/1975 | Harvey et al. | 424/57 |
| 4,036,950 | 7/1977 | Baines et al. | 424/54 |
| 4,123,517 | 10/1978 | Baines et al. | 424/57 |
| 4,130,636 | 12/1978 | Tomlinson | 424/52 |

OTHER PUBLICATIONS

Merck Index, Merck & Co. 9th ed. 1976, Rahway, N.J., p. 1116, entry #8392 "Sodium Lauryl Sulfate".

*Primary Examiner*—Shep K. Rose
*Attorney, Agent, or Firm*—Robert L. Stone; Murray M. Grill; Herbert S. Sylvester

[57] ABSTRACT

A clear gel dentifrice containing "narrow cut" alkali metal lauryl sulphate in which the $C_{12}$ content is at least 90% by weight of the total alkyl content and a fluorine providing compound. The dentifrice contains a further anionic surface active agent which is a substantially saturated higher aliphatic acyl amide of a lower aliphatic amino carboxylic acid salt, a substantially saturated higher fatty aliphatic alcohol alkylene oxide sulphate or a mixture of mono- and di- phosphate esters.

12 Claims, No Drawings

DENTIFRICES

This invention relates to dentifrices of the clear gel type.

Sodium lauryl sulphate is sometimes used as a surface active ingredient in dentifrices. Sodium lauryl sulphate can be produced by the treating the mixture of alcohols obtained by hydrogenation of coconut oil with sulphuric acid, followed by neutralising the product with sodium hydroxide. The product thereby obtained typically contains a broad distribution alkyl chain lengths, such as up to 8% $C_{10}$; at least 50% $C_{12}$; at least 19% $C_{14}$; up to 11% $C_{16}$; and up to 12% $C_{18}$. For producing sodium lauryl sulphate for use as a dentifrice ingredient, the foregoing procedure is sometimes modified to purify the alcohol mixture prior to sulphonation to obtain a "narrow cut" sodium lauryl sulphate in which the $C_{12}$ content is at least 90%, even about 99%. This has raised no problem in opaque dentifrices. However, when a clear gel dentifrice is prepared containing a "narrow cut" sodium lauryl sulphate and a water-soluble alkali metal fluoride or monofluorophosphate, undesirable haziness or cloudiness may occur.

This invention enables haziness or cloudiness of clear gel dentifrices containing "narrow cut" sodium or other alkali metal lauryl sulphate to be reduced. The term "narrow cut" as used herein means that the $C_{12}$ content of the alkali metal lauryl sulphate is at least 90% by weight of the total alkyl content thereof.

According to the invention a clear dentifrice comprises a dentifrice vehicle containing from 5% to 50% of a polishing agent having an empirical $SiO_2$ content of at least 70%, a particle size in the range from 1 to 35 microns, preferably from 2 to 20 microns, an essentially amorphous X-ray structure and an index of refraction between 1.44 and 1.47, a liquid phase having an index of refraction matching that of the polishing agent to permit clarity of the dentifrice, the liquid phase including humectant, a solid phase including a gelling agent or a thickening agent or a mixture thereof, a compound which provides from 0.01% to 1% fluorine, selected from alkali metal fluorides and alkali metal monofluorophosphates, and from 0.1% to 5% of a surface active system comprising narrow cut alkali metal lauryl sulphate and a further anionic surface active agent selected from (a) alkali metal salts of a substantially saturated higher aliphatic acyl amide of a lower aliphatic amino carboxylic acid compound, (b) alkali metal salts of a substantially saturated higher fatty aliphatic alcohol alkylene oxide sulphate, (c) anionic phosphate esters comprising a mixture of a monoester of the formula

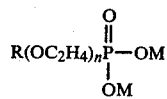

and a diester of the formula

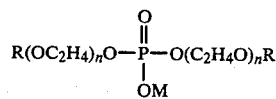

wherein R is an alkyl group of from 10 to 20 carbon atoms, n is an integer from 1 to 6 and M is hydrogen, an alkali metal or ammonium and (d) mixtures thereof, the amount of the alkali metal lauryl sulphate being greater than the amount of the further anionic surface active agent, the ratio being at least 3:1, e.g. about 20:1.

All proportions and amounts herein are by weight.

The proportion of the polishing agent is preferably in the range from 10% to 30%, such as from 15% to 25%. A suitable abrasive is an amorphous alkali metal or alkaline earth metal aluminosilicate having a refractive index in the range from 1.44 to 1.47, and containing at least 70% of silica, up to 10% of alumina, up to 20% of moisture and up to 10% of sodium oxide. This material preferably has a particle size in the range from 2 to 20 microns, e.g. from 2 to 4 microns. The preferred moisture content is from 10% to 20% measured by loss at 1000° C., and the typical content of sodium oxide is from 5% to 10%. Generally, the polishing agent has a loose bulk density of up to 0.2 g/cc, such as from 0.07 to 0.12 g/cc. Another suitable type of polishing agent is porous amorphous silicic anhydride having an average particle size preferably below 20 microns and above 2 microns, a surface area of at least 200 $m^2/g$, preferably at least 300 $m^2/g$, and a bulk density of at least 0.15 $g/cm^3$, preferably at least 0.30 $g/cm^3$, such as a dehydrated silica hydrogel (i.e. a xerogel), preferably of the regular density or intermediate density type. Examples of such amorphous silicic anhydride polishing agents are "Syloid 63", "Syloid 72" and "Syloid 74" which are described in "The Davison Family of Syloid Silicas" published by their manufacturer, Grace, "Davison Chemical Company;" Santocel 100", of Monsanto, is also a desirable dental abrasive (SYLOID and SANTOCEL are trade marks). "Syloid 72" has an average particle size of about 4 microns, a surface area of about 340 $m^2/g$ and a bulk density of about 1.77 $g/cm^3$. "Syloid 74" has an average particle size of about 8 microns, a surface area of about 320 $m^2/g$ and a bulk density of about 0.26 $g/cm^3$. For "Syloid 63" the corresponding figures are about 9 microns, about 675 $m^2/g$ and about 0.4 $g/cm^3$. These amorphous silicic anhydrides may be used singly or in mixtures.

The dentifrice may be a clear toothpaste of a consistency such that it can be extruded from a collapsible tube such as an aluminium tube or a lead tube. The vehicle contains liquid and solids. The liquid phase includes a humectant such as glycerine, aqueous sorbitol or polyethylene glycol, and will usually also include water. The total liquid content of a visually clear dentifrice is generally from 20% to 94.38% and typically comprises glycerine and includes 0 to 10% of water and 0 to 80% of sorbitol. Preferably 0 to 5% of water, 15 to 40% by weight of glycerine and 0 to 50% by weight of sorbitol are present. In the liquid portion of the vehicle, sorbitol is suitably employed as a 70% by weight aqueous solution which has a refractive index of 1.45. Glycerine alone or admixed with the sorbitol solution does not substantially alter this desirable refractive index from that of the polishing agent, since glycerine has a refractive index of 1.47. Thus, an aqueous mixture of sorbitol and a substantial amount of glycerine gives an eminently satisfactory match to the refractive index of the polishing agent.

The solid portion of the vehicle is a gelling agent, such as a natural or synthetic gum or gum-like material, such as Irish Moss, gum tragacanth, alkali metal carboxyvinyl polymers such as those sold as "Carbopol 934" and "Carbopol 940", and synthetic inorganic silicated clays such as those sold as "Laponite CP" and "Laponite SP" (CARBOPOL and LAPONITE are trade marks). These grades of "Laponite" have the formula $(Si_8Mg_{5.4}Li_{0.6}O_{24})^{0.6-}Na_{0.6}^+$. The solid portion of the vehicle is typically present in an amount to about 10% of the dentifrice, preferably from 0.5% to 5%. When employed, grades of "Laponite" are preferably used in an amount from 1% to 5%.

Synthetic finely divided silicas such as those sold as "Cab-O-Sil M-5," "Syloid 244," "Syloid 266," "Aerosil D200" and mixtures thereof may also be employed, e.g. in amounts of from 0.5% to 20%, to promote thickening or gelling and to improve clarity of the dentifrice (CAB-O-SIL, SYLOID and AEROSIL are trade marks).

The dentifrices of the present invention also contain an alkali metal fluoride or monofluorophosphate as a fluoride-containing compound having a beneficial effect on the care and hygiene of the oral cavity, e.g. diminution of enamel solubility in acid and protection of the teeth against decay. Examples are sodium fluoride, potassium fluoride, sodium monofluorophosphate and potassium monofluorophosphate. These materials, which dissociate or release fluorine-containing ions in water, are present in an effective non-toxic amount in the range from 0.01% to 1% as the water-soluble fluorine content thereof.

The surface active system is present in an amount from 0.1% to 5%. The system comprises narrow cut alkali metal lauryl sulphate and a further anionic surface active agent. Non-dodecyl hydrocarbon groups which may be present in small amount include alkyl groups containing 10, 14, 16 and 18 carbon atoms. The narrow cut alkali metal lauryl sulphate is present in greater weight than the further anionic surface active agent, in a ratio from 3:1, typically about 20:1.

The alkali metal salts of the substantially saturated higher aliphatic acyl amides of lower aliphatic amino carboxylic acid compounds which may be used as the further anionic surface active agent include those having 12 to 16 carbons in the fatty acid, alkyl or acyl radicals, and may be, for example, sodium, potassium and ethanolamine salts of N-lauroyl, N-myristoyl and N-palmitoyl sarcosinates which should be substantially free from soap or similar higher fatty acid material which tends to substantially reduce the effect of these compounds. The use of these sarcosinate compounds in the dentifrices of the present invention is particularly advantageous since these materials exhibit a prolonged and marked effect in the inhibition of acid in the oral cavity due to carbohydrates, in addition to exerting some reduction in the solubility of tooth enamel in acid solutions.

The alkali metal salts of the substantially saturated higher fatty alcohol alkylene oxide sulphate compounds which may be used as the further anionic surface active agent include those with alcohol moieties having 12 to 16 carbons (12 and 14 being preferred) and from 1 to 10 alkylene oxide groups wherein the alkylene groups contain 1 to 4 carbon atoms, ethylene oxide as a repeating group, 2 to 3 times, being preferred. The preferred compounds of this class are sodium lauryl ether sulphates, such as $C_{12}$-$C_{14}$ alcohol (ethylene oxide) 2-3:1 sodium sulphate. The compounds may be characterised as having the formula $R'O(C_mH_{2m}O)_qOSO_3X$ wherein $R'$ is an alkyl group containing from 12 to 16 carbon atoms, m is from 1 to 4, q is from 1 to 10 and x is an alkali metal.

The anionic phosphate esters which may be used as the further surface active agent are mixtures of monoesters and diesters of the formulae above set forth. Such ester mixtures are available from MoDo Kemi Aktiebolaget, formerly Berol Aktiebolaget, of Sweden under the name "Berol" and may include an anionic triester moiety too, as well as some non-ionic portion. "Berol 729" has alkyl chain lengths of 16 to 18 carbon atoms and contains series of 4 ethylene oxide units. Since the acid form of "Berol 729" typically provides a completed dentifrice with a pH below 6, this material is generally used in neutralised or partially neutralised form in order to assure a pH above 6 for the completed dentifrice.

Further anionic phosphate esters which may be used in acid or neutralized forms are "Berol 525" which contains alkyl groups of from 10 to 18 carbon atoms and series of 5 ethylene oxide units and "Berol 513" which contains alkyl groups of from 16 to 18 carbon atoms. Use of "Berol 525" in acid form may provide a completed dentifrice with a pH below 6 and it is preferred to use it in neutralized or partially neutralized form. Further "Berol" anionic phosphate esters are available as "Berol 521," "Berol 724" and "Berol 733."The ratio of monoester to diester may vary, typically from 1:10 to 10:1.

When the acid forms of the anionic phosphate ester surface active agents are neutralized or partially neutralized, alkali metal, preferably sodium, or ammonium cations are present.

In addition to the narrow cut alkali metal lauryl sulphate and the further anionic surface active agent, the dentifrice may contain other suitable surface active agents so long as the narrow cut sodium lauryl sulphate and further anionic surface active agent constitute at least 0.1% of the dentifrice, preferably from 1.5% to 2.5% of the dentifrice.

Other suitable surface active materials include nonionic agents such as condensates of sorbitan monostearate with approximately 20 moles of ethylene oxide; condensates of ethylene oxide with propylene oxide condensates of propylene glycol ("Pluronics"—PLURONIC is a trade mark) and cationic surface active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly)oxyethylene groups attached to the nitrogen (typically containing a total of from 2 to 50 ethenoxy groups per molecule) and salts thereof with acids, and compounds of the structure

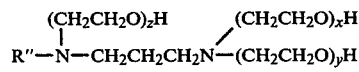

where R" is a fatty alkyl group containing from 12 to 18 carbon atoms and x, y and z total 3 or higher, as well as salts thereof with mineral or organic acids.

Any suitable flavouring or sweetening materials may be employed in formulating a flavour for the dentifrices. Examples of suitable flavouring constituents include flavouring oils, e.g. oils of spearmint, peppermint wintergreen, sassafras, clove, sage, eucalyptus, majoram, cinnamon, lemon and orange, as well as methylsalicylate. Suitable flavouring and sweetening agents may together comprise from 0.01% to 5% or more of the dentifrices. Chloroform may also be used.

Various other materials may be incorporated in the dentifrices of this invention. Examples thereof are colouring agents, preservatives, silicones, chlorophyll compounds and ammoniated materials such as urea, diammoniumphosphate and mixtures thereof. Such adjuvants are incorporated in the dentifrices in amounts which do not substantially adversely affect the properties and characteristics desired.

Antibacterial agents may also be present in the dentifrices, e.g. in an amount from 0.01% to 5%.

Typical antibacterial agents include
$N^1$-(4-chlorobenzyl)-$N^5$-(2,4-dichlorobenzyl) biguanide;
p-chlorophenyl biguanide;
4-chlorobenzhydryl biguanide;
4-chlorobenzyhydrylguanylurea;
N-3-lauroxypropyl-$N^5$-p-chlorobenzylbiguanide;
1,6-di-p-chlorophenylbiguanidohexane
1,6-bis(2-ethylhexylbiguanido) hexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

A toothpaste dentifrice may be prepared by forming a gel with the humectant, gum or thickener and sweetener and adding thereto the polishing agent, surface active agents, flavour and water.

The dentifrices should have a pH practicable for use, e.g. from 4 to 10. A moderately acid to neutral pH is preferred, e.g. from 5 to 7.

The following Example illustrates the invention.

EXAMPLE

The following clear toothpastes A–H are prepared, deaerated and placed in aluminium toothpaste tubes:

| Components | Parts | | | | | | | |
|---|---|---|---|---|---|---|---|---|
| | A | B | C | D | E | F | G | H |
| Glycerine | 25.00 | 25.00 | 22.30 | 25.00 | 25.00 | 25.00 | 25.00 | 25.00 |
| Sodium saccharin | 0.17 | 0.17 | 0.17 | 0.17 | 0.17 | 0.17 | 0.17 | 0.17 |
| Sodium carboxymethyl cellulose | 0.17 | 0.19 | 0.20 | 0.20 | 0.19 | 0.20 | 0.20 | 0.20 |
| Sodium monofluorophosphate | 0.82 | 0.82 | 0.82 | 0.82 | 0.82 | 0.82 | 0.82 | 0.82 |
| Sorbitol (70% solution in water) | 41.34 | 42.83 | 41.98 | 43.26 | 42.82 | 43.16 | 43.16 | 40.46 |
| Water - deionised | 3.20 | 3.00 | 1.80 | 3.00 | 2.50 | 2.74 | 1.71 | 3.00 |
| Polyethylene glycol 600 | 3.00 | — | 3.00 | — | — | — | — | 3.00 |
| Colour solution (0.5%) | 0.30 | 0.49 | — | — | 0.49 | — | — | — |
| Colour solution (1%) | — | — | 0.65 | — | — | — | — | — |
| Colour solution (5%) | — | — | — | 0.15 | — | 0.15 | 0.15 | 0.15 |
| Sodium aluminosilicate | 17.00 | 17.00 | 17.00 | 17.00 | 17.00 | 17.00 | 17.00 | 17.00 |
| Silica thickener ("Syloid 244") | 6.00 | 7.50 | 7.20 | 7.50 | 7.50 | 7.50 | 7.50 | 7.20 |
| Flavour | 1.00 | 1.00 | 1.00 | 1.00 | 1.00 | 1.00 | 1.00 | 1.00 |
| Narrow cut sodium lauryl sulphate 99% $C_{12}$ ("Texapon L-100"-Henkel). | 2.00 | 1.80 | 1.50 | 2.00 | 1.80 | 1.90 | 1.50 | 1.50 |
| Sodium-N-lauroyl sarcosinate pellets | — | 0.20 | — | — | — | — | — | — |
| Sodium N-lauroyl sarcosinate solution (21% sarcosinate, 30% glycerine, 49% water) | — | — | 2.38 | — | — | — | — | — |
| Anionic phosphate ester ("Berol 513") | — | — | — | — | — | — | — | 0.50 |
| $C_{12}$—$C_{14}$ alcohol EO 3:1 sodium sulphate (28% solution) | — | — | — | — | 0.71 | 0.36 | 1.79 | — |
| PH | 6.4 | 6.15 | 6.82 | 5.88 | 6.10 | 6.00 | 5.77 | 5.7 |

The dentifrices are aged at room temperature, at 43° C. and at 4° C. Control dentifrice A in which sodium lauryl sulphate is the only anionic surface active agent is hazy after 1 month at 4° C. and slightly hazy after 1 month at room temperature. Control dentifrice D in which also sodium lauryl sulphate is the only anionic surface active agent is hazy after 1 month at 43° C. and slightly hazy after 1 month at room temperature at 4° C. No substantial haze is observed even after 3 months or more at room temperature, 43° C. and 4° C. with dentifrices B, C, F and G, containing mixed anionic surface active agents. There is very slight haze observed with dentifrice E containing a mixed anionic surface active system. However, the haze is less than with the control dentifrices A and D. Dentifrice H ages well without substantial haze.

Modifications of which fall within the scope of the invention may be made. For instance, when 0.2 parts of sodium fluoride is present rather than 0.82 parts sodium monofluorophosphate, the haze is reduced when the further anionic surface active agent is present.

What we claim is:

1. A clear dentifrice comprising a dentifrice vehicle containing from 5% to 50% of a polishing agent having an empirical $SiO_2$ content of at least 70%, a particle size in the range from 1 to 35 microns, an essentially amorphous X-ray structure and an index of refraction between 1.44 and 1.47, a liquid phase having an index of refraction matching that of the polishing agent to permit clarity of the dentifrice, the liquid phase including humectant, a solid phase including a gelling agent or a thickening agent or a mixture thereof, a compound which provides from 0.01% to 1% of fluorine, selected from alkali metal fluorides and alkali metal monofluorophosphates, and from 0.1% to 5% of a surface active system comprising narrow cut alkali metal lauryl sulphate in which the $C_{12}$ content is at least 90% and a further anionic surface active agent selected from (a) alkali metal salts of a substantially saturated higher aliphatic acid amide of a lower aliphatic amino carboxlic acid compound, (b) alkali metal salts of a substantially saturated higher fatty aliphatic alcohol alkylene oxide sulphate, (c) an anionic phosphate esters comprising a mixture of a monoester of the formula

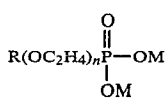

and a diester of the formula

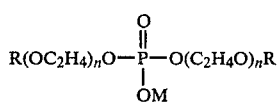

wherein R is an alkyl group of from 10 to 20 carbon atoms, n is an integer from 1 to 6 and M is hydrogen, an alkali metal or ammonium and (d) mixtures thereof, the amount of the alkali metal lauryl sulphate being greater than the amount of the further anionic surface active agent, the ratio being at least 3:1.

2. A clear dentifrice as claimed in claim 1 wherein the ratio of narrow cut alkali metal lauryl sulphate to the further anionic surface active agent is about 20:1.

3. A clear dentifrice as claimed in claim 1 wherein the narrow cut alkali metal lauryl sulphate is narrow cut sodium lauryl sulphate.

4. A clear dentifrice as claimed in claim 1 wherein the liquid phase comprises glycerine, sorbitol solution or a mixture thereof.

5. A clear dentifrice as claimed in claim 1 wherein the solid phase contains sodium carboxymethyl cellulose.

6. A clear dentifrice as claimed in claim 1 wherein the compound providing fluorine is sodium monofluorophosphate.

7. A clear dentifrice as claimed in claim 1 wherein the particle size of the polishing agent is in the range from 2 to 20 microns.

8. A clear dentifrice as claimed in claim 1 wherein the polishing agent is sodium aluminosilicate.

9. A clear dentifrice as claimed in claim 1 wherein the further anionic surface active agent is sodium N-lauroyl sarcosinate.

10. A clear dentifrice as claimed in claim 1 wherein the further anionic surface active agent is a $C_{12-14}$ alcohol (ethylene oxide) 2-3:1 sodium sulphate.

11. A clear dentifrice as claimed in claim 1 wherein the further anionic surface active agent is a said anionic phosphate ester mixture wherein in the formulae of the monoester and the diester R is an alkyl group containing from 16 to 18 carbon atoms.

12. A clear dentifrice as claimed in claim 11 wherein the further anionic surface active agent is a mixture of the sodium salts of the anionic phosphate monoester and diester.

* * * * *